US00PP26051P3

(12) United States Plant Patent
Olesen

(10) Patent No.: US PP26,051 P3
(45) Date of Patent: Nov. 10, 2015

(54) MINIATURE ROSE PLANT NAMED 'POULTY019'

(50) Latin Name: ***Rosa* hybrid**
Varietal Denomination: Poulty019

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 169 days.

(21) Appl. No.: 13/986,937

(22) Filed: Jun. 14, 2013

(65) Prior Publication Data

US 2014/0373205 P1 Dec. 18, 2014

(51) Int. Cl.
*A01H 5/02* (2006.01)

(52) U.S. Cl.
USPC ..... Plt./116

(58) Field of Classification Search
USPC ..... Plt./116, 123, 141

CPC ..... A01H 5/0222; A01H 5/0216; A01H 5/02; A01H 5/00
See application file for complete search history.

(56) References Cited

PUBLICATIONS

Poulsen Roser A/S Perfect your production in 2010 with novelties from Poulsen Roser A/S, retrieved on Jan. 8, 2015, retrieved from the Internet at <www.clamerinforma.it/News/file/PoulsenRoser.pdf> one page.*
Floradania Marketing: floradania.dk Jun. 2010, retrieved on Jan. 13, 2015, retrieved from the Internet at <floadania.dk/en/nyhedsbrev-web/floradaniadk-2010/floradaniadk-062010/> 2 pp.*
Upov Pluto Plant Variety Database 20150114 retrieved on Jan. 14, 2015, retrieved from the Internet <www3.wipo.int/pluto/user/en/index.jsp> for Rosa Poulty019 one page.*

* cited by examiner

*Primary Examiner* — June Hwu

(57) ABSTRACT

A new miniature rose plant that has abundant red flowers with white-pink stripes and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulty019'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulty019', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant red flowers with white-pink stripes;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulty019' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulty019' was selected by the inventor as a single plant from the progeny of the hybridization in 2007.

Asexual reproduction of 'Poulty019' by vegetataive stem cuttings was first done by Mogens N. Olesen in the nursery in Fredensborg, Denmark in 2008. This initial and other subsequent propagations conducted in controlled environments have demonstrated that the characteristics of 'Poulty019' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty019'. Specifically illustrated in the drawing are flowers at various stages of development, flower in parts, leaves, and stems.

DETAILED DESCRIPTION OF THE VARIETY

The following is a description of 'Poulty019', as observed in its growth in glasshouses in Burlington, Ontario, Canada.

Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulpah024', U.S. Plant Pat. No. 18,729 are compared to 'Poulty019' in Chart 1.

CHART 1

| | 'Poulty019' | 'Poulpah024' |
|---|---|---|
| Petalage: | 25 petals total, 3 of which are petaloids | 90 petals, 10 to 15 of which are petaloids |
| Flower Diameter: | 40 mm | 55 to 60 mm |
| General Tonality of Flower Color: | Red Group 46A splashed with White Group N155B and Red Group 49A. | Red-Purple Group 57A with streaks of White Group 155A and Yellow Group 5D |

Flower and Flower Bud

Blooming habit: Continuous.

Flower bud:

*Size*.—Upon opening, 18 mm in length from base of receptacle to end of bud. 11 mm in diameter.

*Bud form*.—

*Bud color*.—As sepals unfold, petals are Red Group 53A splashed with Orange Group 27C.

*Sepals*.—Upper Surface: Color: Green Group 138B. Texture: Smooth, moderately pubescent. Lower Surface: Color: Yellow Green Group 144A. Texture: Smooth. Shape: Apex: Cirrhose. Base: Flat at union with receptacle. Margins: Margins have weak to moderate foliaceous appendages on three of the five sepals. Size: 25 mm long by 7 mm wide.

*Receptacle*.—Surface Texture: Smooth. Shape: Campanulate. Size: 7 mm tall and 11 mm wide. Color: Yellow Green Group 144A.

*Pedicel*.—Surface: Smooth with many stipitate glands. Length: 20 mm on average. Diameter: Generally 3 mm. Color: Yellow-Green Group 144A. Strength: Strong.

*Borne*.—Singly.

Flower bloom:

*Fragrance*.—Light floral scent.

*Duration*.—As a pot plant, flowers last up to 28 days.

*Size*.—Flower diameter is 40 mm when open. Flower depth is 15 mm.

*Form*.—General shape is a rosette.

*Shape of flower, side view*.—Upon opening, the upper portion is convex. The lower portion is flat.

Petalage: Semi-double. Under normal conditions, flowers have 25 petals total, 3 of which are petaloids.

Color:

*General tonality*.—On open flower Red Group 46A splashed with White Group N155B and Red Group 49A. General tonality does not change.

*Upon opening, petals*.—Upper surface is Red Group 46A splashed with White Group N155B and Red Group 49A. Lower surface is Red Group 53A splashed with White Group N155B and Red Group 49A.

*After opening, petals*.—Upper surface is Red Group 46A splashed with White Group N155B and Red Group 49A. Lower surface is Red Group 53A splashed with White Group N155B and Red Group 49A.

Petals:

*Petal reflex*.—Strong.

*Margin*.—Entire.

*Shape*.—Generally broad elliptic. Apex shape: Rounded. Base shape: Acute.

*Size*.—19 mm (l) by 18 mm (w).

*Texture*.—Smooth.

*Thickness*.—Average.

Petaloids:

*Quantity*.—3 on average.

*Shape*.—Irregular, and asymmetric. The apex and base are acute.

*Color*.—Upper surface is Red Group 46A splashed with White Group N155B and Red Group 49A. Lower surface is Red Group 53A splashed with White Group N155B and Red Group 49A.

*Size*.—13 mm (l) by 6 mm (w).

Reproductive organs:

*Pollen*.—None Observed.

*Anthers*.—Size: 2 mm long. Color: Yellow-Orange Group 14D. Quantity: 30 on average.

*Filaments*.—Color: Orange Red Group 35B. Length: About 4 mm.

*Pistils*.—Length: About 3 mm long. Quantity: 15 on average.

*Stigmas*.—Slightly inferior relative to the length of the filaments and the height of the anthers. Color: Yellow-White Group 158A.

*Styles*.—Color: Green-White Group 157B.

*Seed formation*.—Not observed.

Plant

Plant growth: Upright. Plants are 17 cm in height, and 15 cm wide.

Stems:

*Color*.—Juvenile growth: Yellow-Green Group 146B. Mature growth: Yellow-Green Group 146A.

*Length*.—Canes are 13 cm from the base of the plant to the flowering portion.

*Diameter*.—2 mm.

*Internodes*.—On mature canes, there is an average distance of 15 mm between nodes.

*Surface texture*.—Young and mature wood is smooth.

Prickles:

*Incidence*.—1 or 2 per 10 cm of stem.

*Size*.—Average length: 2 mm.

*Color*.—Prickles are Greyed-Yellow Group 160C.

*Shape*.—Linear.

Plant foliage:

*Compound leaf size*.—75 mm (l) by 43 mm (w).

*Quantity*.—4 leaves per 10 cm of stem on average.

*Color of juvenile foliage*.—Upper Leaf Surface: Yellow-Green Group 144B. Lower Leaf Surface: Yellow-Green Group 144B.

*Color of mature foliage*.—Upper Leaf Surface: Yellow-Green Group 147A. Lower Leaf Surface: Yellow-Green Group 147B.

Plant leaves and leaflets:

*Stipules*.—Size: About 3 mm in length. Shape: Linear, slightly broad based with outward extending apecies.

Margins: Finely serrated with few stipitate glands. Color: Yellow-Green Group 144A.

*Petiole*.—Length: 15 mm on average. Diameter: About 1 mm. Upper surface: Yellow-Green Group 146A. Lower surface: Yellow-Green Group 146C.

*Rachis*.—Length: 25 mm on average. Diameter: About 2 mm. Upper surface: Yellow-Green Group 146A. Lower surface: Yellow-Green Group 146C.

*Leaflet*.—Number of leaflets: 5 on normal leaves in middle of the stem. Size: 31 mm in length by 15 mm wide. Margin: Serrate. General Shape: Elliptical. Apex Shape: Acute. Base Shape: Round. Texture: Smooth. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

Disease resistance: Above average resistance to powdery mildew *Sphaerotheca pannosa,* downy mildew *Peronospora sparsa,* rust *Phragmidium* sps., black spot *Diplocarpon rosae,* and *Botrytis cinerea* under normal growing conditions.

The invention claimed is:

1. A new and distinct variety of rose plant of the miniature class named 'Poulty019', illustrated and described herein, due to its abundant, red flowers with white-pink stripes, vigorous growth, compact habit, suitability for production from softwood cuttings in pots, and durable flowers and foliage that make the variety suitable for distribution in the floral industry.

* * * * *

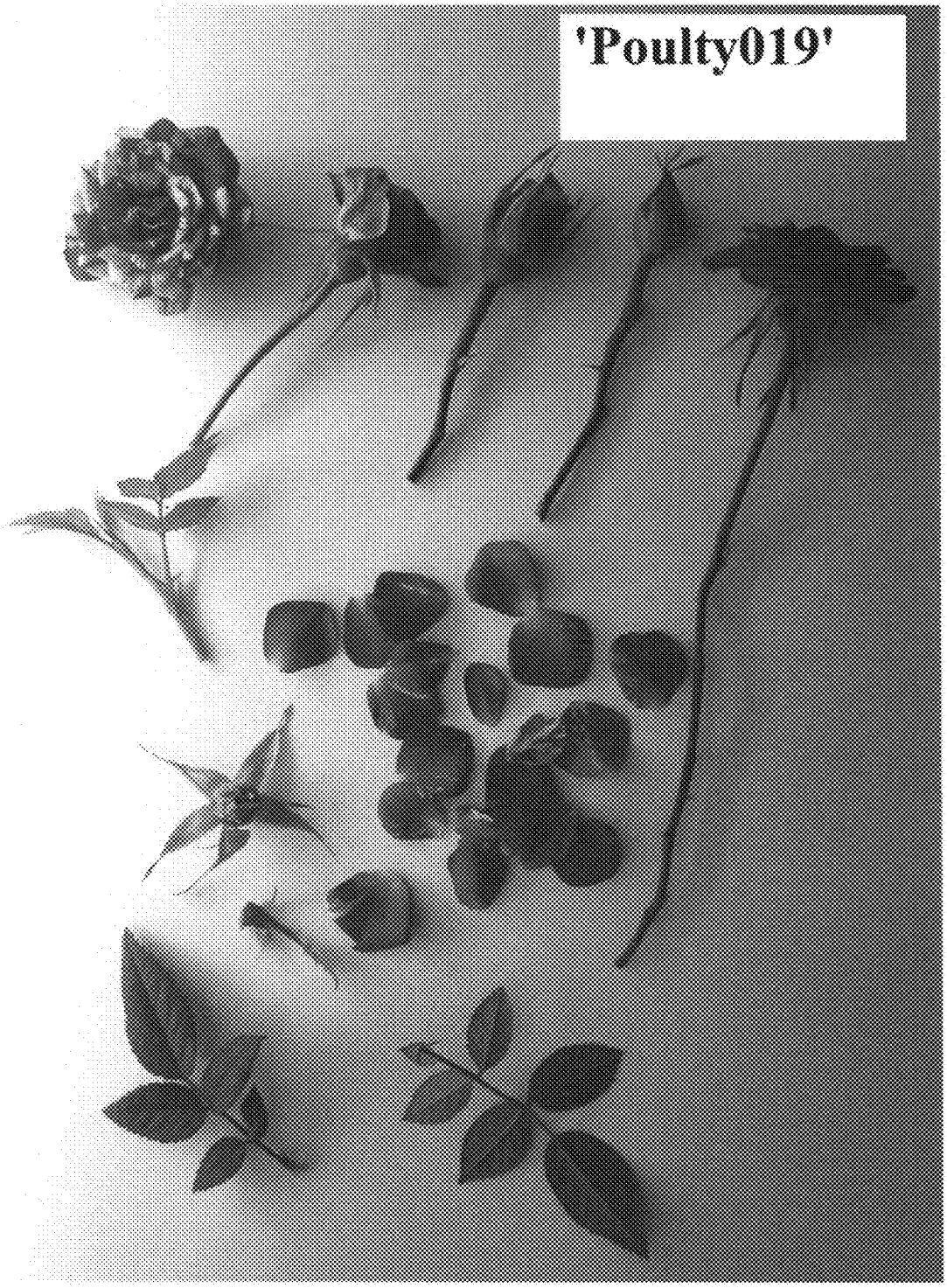
'Poulty019'